(12) United States Patent
Anderson et al.

(10) Patent No.: US 6,998,095 B2
(45) Date of Patent: Feb. 14, 2006

(54) LOOP DILUTION SYSTEM

(75) Inventors: Marc R. Anderson, Sunnyvale, CA (US); Michael J. West, Sunnyvale, CA (US); James Tappan, Sunnyvale, CA (US)

(73) Assignee: Metara, Inc., Sunnyvale, CA (US)

( * ) Notice: Subject to any disclaimer, the term of this patent is extended or adjusted under 35 U.S.C. 154(b) by 0 days.

(21) Appl. No.: 10/641,480

(22) Filed: Aug. 15, 2003

(65) Prior Publication Data

US 2005/0037517 A1    Feb. 17, 2005

(51) Int. Cl.
*B01L 11/00* (2006.01)

(52) U.S. Cl. ......................................... 422/103; 422/81
(58) Field of Classification Search .................. 422/81, 422/103; 73/866; 436/54
See application file for complete search history.

(56) References Cited

U.S. PATENT DOCUMENTS

| | | |
|---|---|---|
| 4,036,062 A | 7/1977 | Cruzan |
| 4,095,472 A | 6/1978 | Mowery, Jr. |
| 4,186,607 A | 2/1980 | Porter et al. |
| 4,271,697 A | 6/1981 | Mowery, Jr. |
| 6,153,437 A | 11/2000 | Horn |
| 6,526,811 B1 | 3/2003 | Johnson et al. |
| 2004/0168529 A1 * | 9/2004 | Carlson et al. ............... 73/866 |

* cited by examiner

*Primary Examiner*—Yelena G. Gakh
(74) *Attorney, Agent, or Firm*—Jonathan W. Hallman; MacPherson Kwok Chen & Heid

(57) ABSTRACT

A loop dilution system includes a dual-loop multi-way valve. In a first configuration of the multi-way valve, a first loop may be filled with a first solution and a second loop may be filled with a second solution. In a second configuration of the multi-way valve, the first and second loops are serially connected with a pump so that their contents may be mixed with a diluent. In another aspect of the invention, an in-process mass spectrometry (IPMS) system is disclosed that uses an internal standard to determine the concentration of an analyte in a sample. The internal standard has a different molecular composition than the analyte but is sufficiently similar chemically and physically to the analyte such that it behaves substantially the same as the analyte during an ionization process in the mass spectrometer.

9 Claims, 4 Drawing Sheets

LOOP DILUTION SYSTEM

TECHNICAL FIELD

The present invention relates generally to chemical analysis, and more particularly to apparatus for the mixing and dilution of a first and a second solution. In addition, the present invention relates generally to in-process mass spectrometry (IPMS) and more particularly to an IPMS process using an internal standard having a different molecular composition than the analyte of interest.

BACKGROUND

Automated systems for measuring the concentration of analytes in a sample have been developed using a number of analytical techniques such as chromatography or mass spectrometry. In particular, mass spectrometry is often the technique of choice to achieve sensitivity of parts per billion (ppb) or sub-ppb such as parts per trillion (ppt). For example, co-assigned U.S. patent application Ser. No. 10/086,025 (the '025 application) discloses an automated analytical apparatus measuring contaminants or constituents in trace concentrations.

In an Isotope Dilution Mass Spectrometry (IDMS) technique, a sample of interest is spiked, i.e., has added to it a known amount of the appropriate isotopic species. In measuring trace concentrations, the spike source will generally be stored at a relatively high concentration and must then be diluted before use. Accordingly, the '025 application discloses a dilution module tat includes a reservoir of spike solution stored at a stable, relatively high concentration. A syringe pump is used to remove a portion of spike from the reservoir, which is then mixed with a diluent sample in a mixer. Because the automated apparatus disclosed in the '025 application was directed to the measurement of constituents or contaminants at trace concentrations, there was no need to dilute the sample before mixing it with the spike.

However, there are applications in which dilution of the sample is necessary. For example, copper processing in semiconductor manufacturing uses a relatively comprises a relatively concentrated acidic aqueous copper sulfate solution. Plating topology is controlled by organic plating solution additives within the copper sulfate solution that function to either suppress or accelerate the plating process. These additives experience electrochemical breakdown during the plating process and can be lost by drag out or by becoming trapped within the film. However, the achievement of void-free plating in the vias and trenches of sub-micron high-aspect-ratio structures requires very tight control of additive levels. Unlike indirect measurement methods such as cyclic voltametric stripping (CVS) that monitor the effectiveness of the plating solution, the IPMS apparatus discussed above allows a user to directly measure the additive concentration plus the breakdown products in the electroplating bath to ensure a defect-free deposition process.

Since the electroplating process takes place under clean room conditions, automation to minimize human interaction with the metrology tool is critical. The in-process mass-spectrometry (IPMS) apparatus disclosed in the '025 application meets this automation need but does not provide a capability to dilute the sample and spike simultaneously. Moreover, the dilution module disclosed in the '025 application uses a syringe pump to draw a portion of the spike prior to its dilution. Because of mechanical vagaries, a syringe pump will not necessarily draw the same amount for each portion, thereby adversely affecting measurement precision. In contrast, loop dilution techniques avoid this imprecision through the use of two-position multi-way valves.

Figure 1:
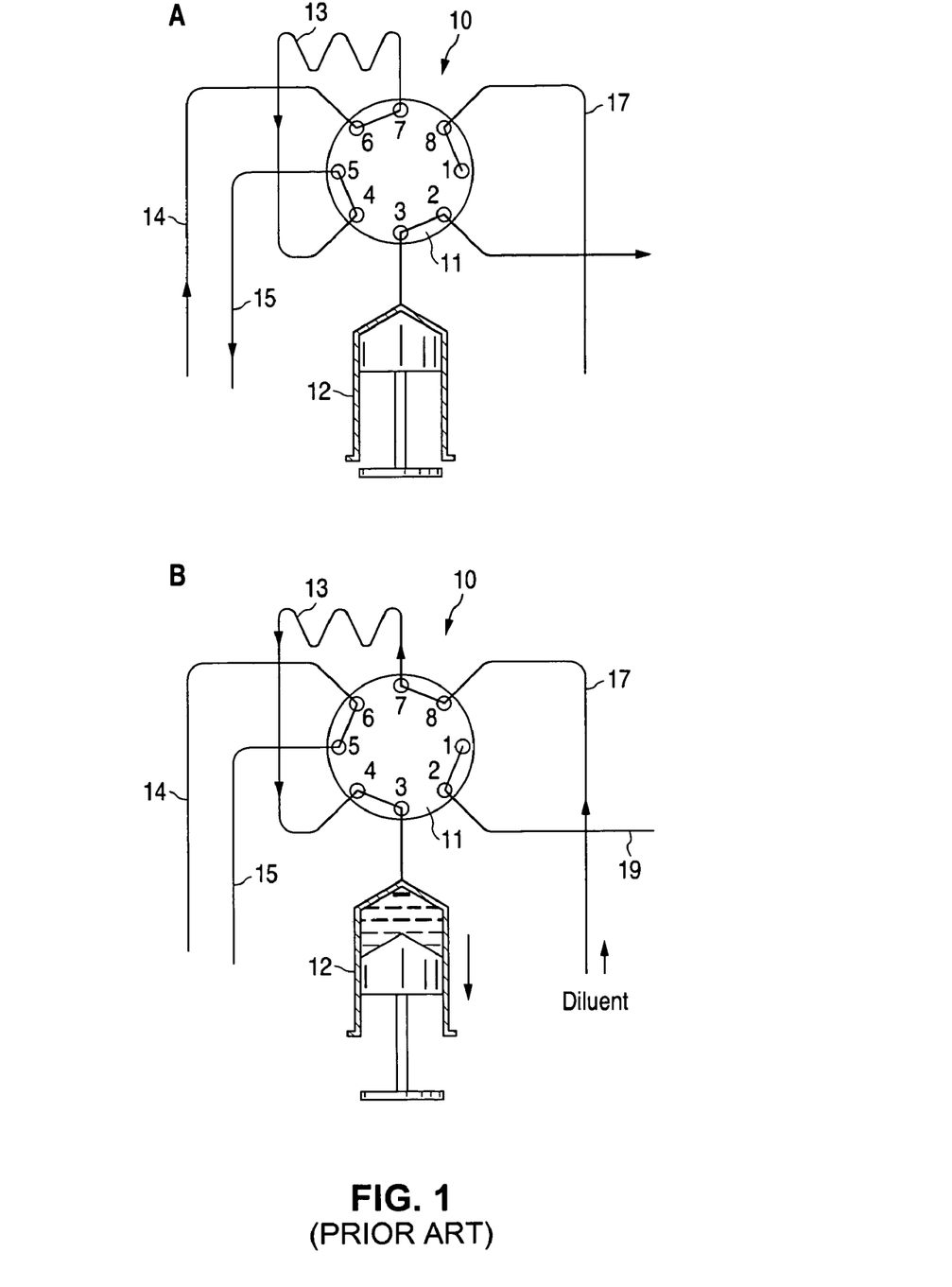
FIG. 1a is a schematic representation of a conventional loop dilution valve in a load and delivery phase.
FIG. 1b is a schematic representation of a conventional loop dilution valve in a mixing phase.

A conventional two-position eight-way valve 10 is shown in FIGS. 1a and 1b. Each way or port of valve body 11 is numbered, starting from port 1 through port 8. A loop or fluid conduit 13 keeps ports 7 and 4 connected (in fluid communication). Depending upon whether valve 10 is in a load and delivery position as seen in FIG. 1a or in a mix position as seen in FIG. 1b, similar fluid connections between other ports may be changed. For example, in the loading position (FIG. 1a), ports 6 and 7 are in fluid communication whereas in the mix position (FIG. 1b) ports 6 and 7 are in fluid communication with ports 5 and 8, respectively. Port 1 is closed in both phases. During the loading phase shown in FIG. 1a, loop 13 is filled with the solution-to-be-diluted by pumping into port 6 from a solution source (not shown) connected to line 14 which in turn is connected to port 6. To ensure a clean sample within loop 13, this pumping continues for a sufficient amount of time to flush any previous solution within loop 13 out through port 4 into port 5 which in turn is connected to an output line 15. Note the advantages of such a loading phase: the internal volume of loop 13 is static and thus the volume of solution loaded into loop 13 will be constant for each loading stage or cycle. This fixed volume of solution stored within loop 13 will then be diluted in the loading stage shown in FIG. 1b. In this loading stage, one end of loop 13 is now connected to syringe pump 12 through port 3. The remaining end of loop 13 connects to a conduit 17 connected to a diluent source (not illustrated) through port 8. Thus, as the plunger in syringe pump 12 is withdrawn, turbulent mixing of the solution which had filled loop 13 with the diluent drawn through port 8 occurs within syringe pump 12. This mixing is aided by a reciprocating movement of the plunger. Because syringe pump 12 may be controlled by a stepper motor, the volume of the fluid withdrawn into syringe pump 12 may be fairly precisely reproduced during subsequent mixing phases. Finally, valve 10 returns to the loading and delivery position of FIG. 1a so that the plunger of syringe pump 12 may be depressed, thereby pumping the diluted solution out through port 2.

Although the loop dilution technique described with respect to FIGS. 1a and 1b are efficient and reasonably precise, conventional loop dilution valves do not allow a user to simultaneously mix and dilute two different solutions (such as a sample and a spike in an IPMS process). Accordingly, there is a need in the art for improved loop dilution valves and techniques permitting the precise mixing and simultaneous dilution of two different solutions.

Such an improved loop dilution valve may be used in an in-process mass spectrometry (IPMS) system to mix and dilute sample and spike before analysis. An automated IPMS system is described in co-assigned U.S. patent application Ser. No. 10/094,394, entitled "A Method and Apparatus for Automated Analysis and Characterization of Chemical Constituents of Process Solutions," filed Mar. 8, 2002, the contents of which are hereby incorporated by reference in their entirety. Although the IPMS technique provide accurate results, it may require the use of enriched isotopes of the species to be analyzed. Enriched isotopes are generally quite expensive, making continuous analysis expensive. Accordingly, there is another need in the art for improved mass spectrometry techniques that do not require the use of enriched isotope spikes.

SUMMARY

In accordance with the present invention, an automated dilution module which meets the need of metrology tools to simultaneously mix and dilute two solutions is provided as well as a method to achieve this result. Accordingly, one aspect of the invention relates to an analytical apparatus including a first pump; a first loop having a predetermined volume; a second loop having a predetermined volume; and a multi-path valve, wherein the multi-path valve has a first configuration connecting a first end of the first loop to a first solution source and connecting a first end of the second loop to a second solution source, and wherein the multi-path valve has a second configuration serially connecting the first loop to the second loop and connecting the first pump to a first end of the serially-connected loops. In a loading configuration, the multi-path valve enables the simultaneous loading of a first solution into the first loop and a second solution into the second loop. In the mixing configuration, the multi-path valve enables the first pump to pump diluent through the serially connected loops to simultaneously mix and dilute the contents of the first and second loops. Because the predetermined volume for the first and second loops is constant, by cycling the multi-path valve between the loading and mixing configurations, the analytical apparatus may precisely dilute and mix known volumes of the first and second solutions.

BRIEF DESCRIPTION OF THE DRAWINGS

Use of the same reference symbols in different figures indicates similar or identical items.

DETAILED DESCRIPTION

Figure 2:
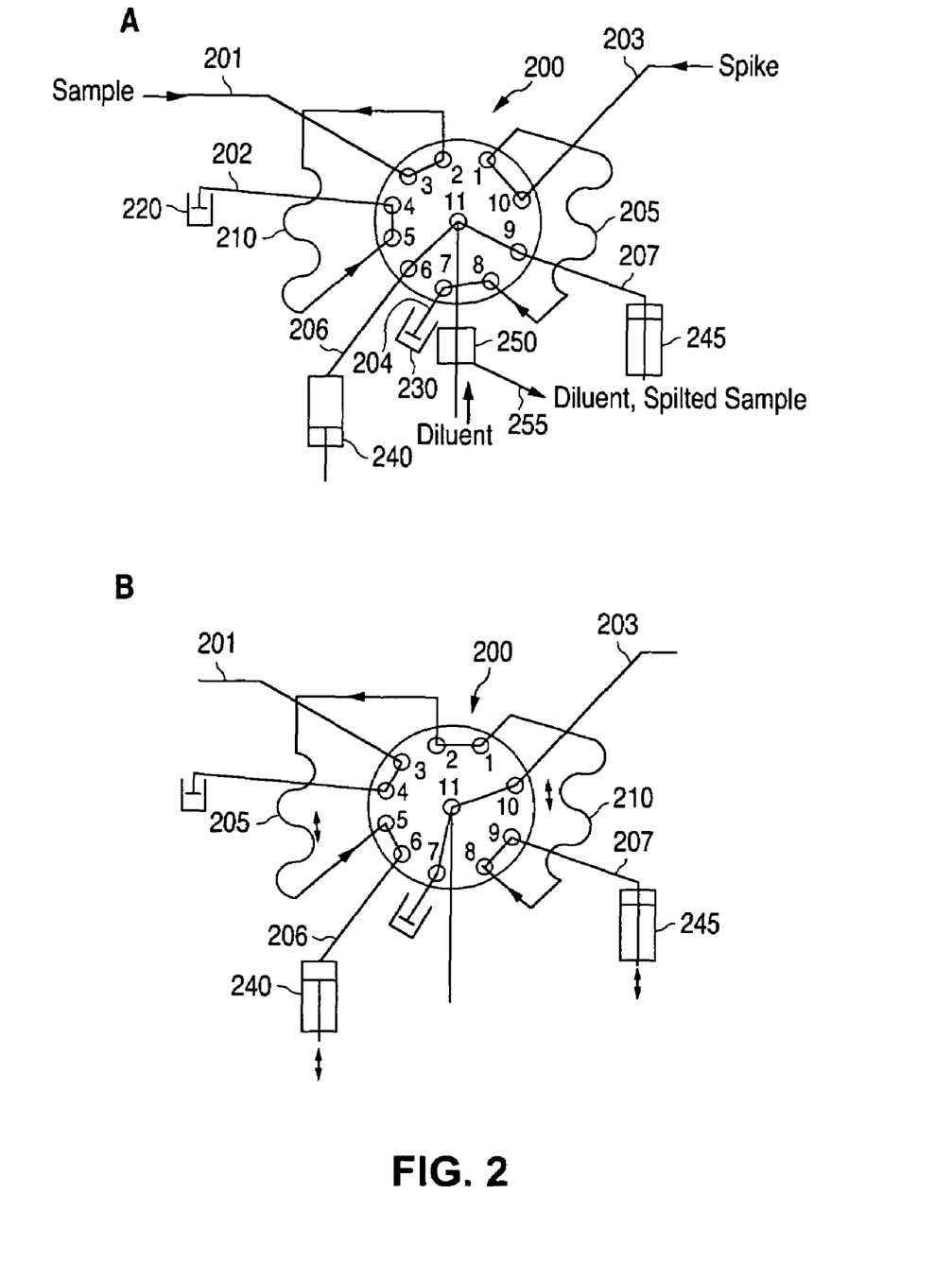
FIG. 2a is a schematic representation of a two-position multi-way loop dilution valve having two loops in a fill and deliver configuration according to one embodiment of the invention.
FIG. 2b is a schematic representation of the two-position multi-way loop dilution valve of FIG. 2a in a mixing configuration according to one embodiment of the invention.

The present invention provides a dilution module that enables the simultaneous mixing and dilution of two different solutions using a novel two-position multi-way valve. Turning now to FIGS. 2a and 2b, an exemplary embodiment for this two-position multi-way valve 200 is illustrated. Valve 200 has 11 ports numbered 1 through 11, with port 11 being in the center of valve 200 rather than on its periphery as is the case for ports 1 through 10. Depending upon the valve configuration, these ports are connected (in fluid communication) as 4 pairs in different fashions. In addition, a different pair of ports connects with port 11 in each configuration to form a port triplet, i.e, a connection of three ports. In the fill and delivery configuration illustrated in FIG. 2a, the ports are paired as follows: 1-10, 2-3, 4-5, and 7-8. In this fill and delivery configuration, ports 6, 9, and 11 are all connected to form the triplet. However, in the mixing configuration illustrated in FIG. 2b, the ports are paired differently: 1-2, 3-4, 5-6, and 8-9. Ports 7, 11, and 10 form the triplet. Regardless of the configuration, a fluid conduit or loop 205 connects ports 8 and 1. Similarly, a fluid conduit or loop 210 connects ports 2 and 5. Valve 200 includes a rotor (not illustrated) having laminar grooves that effect the connections between the ports in the various configurations. A motor or actuator (not illustrated) spins the rotor between fixed positions to switch valve 200 between the fill and delivery and the mixing configurations.

When valve 200 is in the fill and delivery configuration, a first solution is pumped into port 3 from a conduit 201 fed by a first solution source (not shown) to fill loop 210. In an IPMS application, this first solution may comprise the sample to be analyzed. To ensure an uncontaminated sample, an adequate volume of the first solution is pumped into port 3 to flush any pre-existing solution within loop 210 into drain 220 connected to port 4 by a conduit 202. During this same configuration, loop 205 is filled with a second solution pumped into port 10 from a conduit 203 fed by a second solution source (not illustrated). In an IPMS application, this second solution may comprise the spike. Loop 205 may be flushed through port 7 and a conduit 204 into drain 230 in the same manner as described for loop 210 to ensure the second solution filling loop 205 is uncontaminated. Syringe pumps 240 and 245 connect through ports 6 and 9 to port 11, respectively, in the fill and delivery configuration. Diluent may be pumped into port 11 from a diluent source (not illustrated) to fill either or both of syringes 240 and 245. Because syringes 240 and 245 may be operated by stepper motors (not illustrated) as is known in the art, a precise amount of diluent may be loaded into either syringe at this time. Each stepper motor withdraws the plunger in its respective syringe by a known amount, thereby allowing a predetermined amount of diluent to fill the syringe.

Having loaded loops 205 and 210 and one or both of syringes 240 and 245, valve 200 may switch to the mixing configuration shown in FIG. 2b. In this configuration loops 205 and 210 are connected in series between syringes 240 and 245. As shown in FIG. 2a, syringe 240 has already been loaded with an predetermined volume of diluent. Thus, in the mix configuration of FIG. 2b, diluent will flush the contents of loops 210 and 205 into syringe 245 when the plunger of syringe 240 is depressed (assuming that the plunger of syringe 245 is withdrawn at the same time). Syringe 245 will then contain a largely-homogeneous solution of diluent and the previous contents of loops 205 and 210. If desired, a reciprocating pumping action between syringes 245 and 240 will then ensure that a homogeneous solution is obtained. In each reciprocation cycle, the plunger of one syringe is depressed while the remaining syringe's plunger is withdrawn. To complete the cycle, the remaining syringe's plunger is then depressed while the one syringe's plunger is withdrawn. By completing a number of such reciprocations, a user may be assured that a homogeneous solution has been achieved. For example, a substantially uniform homogeneous solution is typically obtained after 5 reciprocation cycles. Note the advantages of this reciprocating pumping action over the prior art mixing dilution and mixing process described with respect to syringe pump 12 of FIG. 1b. As discussed previously, the plunger of syringe pump 12 may be reciprocated slightly to achieve a more homogeneous solution of diluent and sample. However, because loop 13 remains connected to the diluent source attached to line 17 during these reciprocations, the actual amount of diluent used becomes uncertain and imprecise.

However, this is not the case with the mixing provided by syringe pumps 240 and 245 in FIG. 2b. No additional diluent may enter loops 210 and 205 while syringe pumps 240 and 245 conduct their reciprocating pumping action. Thus, very precise dilution over multiple fill and mix cycles may be achieved.

During a subsequent fill and delivery configuration, the homogeneous diluted solution is pumped by one or both of syringes 240 and 245 through port 11 of multi-way valve 200. Because of the dual role for port 11 in this configuration (diluent flows into port 11 whereas homogeneous diluted solution flows out of port 11), a tree-way valve 250 connects to port 11 as shown in FIG. 2a. In a first configuration for the fill and delivery stage, three-way valve 250 connects port 11 to a diluent source so that syringe 240 and/or syringe 245 may receive a predetermined volume of diluent. In a second configuration for the mixing stage, three-way valve 250 connects port 11 to a fluid conduit 255 so that the homogeneous diluted solution may be provided to a metrology instrument (not illustrated).

The construction of loops 205 and 210 is not important so long as their internal volume is static, i.e., the loops should not be constructed from elastic materials. A wide variety of conventional tubing may thus be used to construct loops 205 and 210. Given a tubing with a well-defined lumen diameter, the length used will determine the volume carried by the resulting loop. In turn, this volume and the amount of diluent withdrawn by each syringe determines the overall dilution ratio. For example, if the length of loop 210 is such that it holds 200 microliters of the first solution and syringe 240 is filled with 4.6 millileters of diluent, an approximate 20:1 dilution ratio may be achieved. The actual dilution ratio also depends upon the volume of the second solution within loop 210. Because of the loop dilution, however, whatever dilution ratio is achieved will be repeatable, lending precision to repeat measurements. It will be appreciated by those of ordinary skill in the art that multi-way valve 200 is merely an exemplary embodiment. The arrangement and number of ports, the type and number of pumps to which it connects, and other features for multi-way valve 200 may all be varied without departing from the scope of the invention. For example, a third loop may be added should a third solution need to be mixed with the final homogeneous and diluted solution.

Figure 3A:
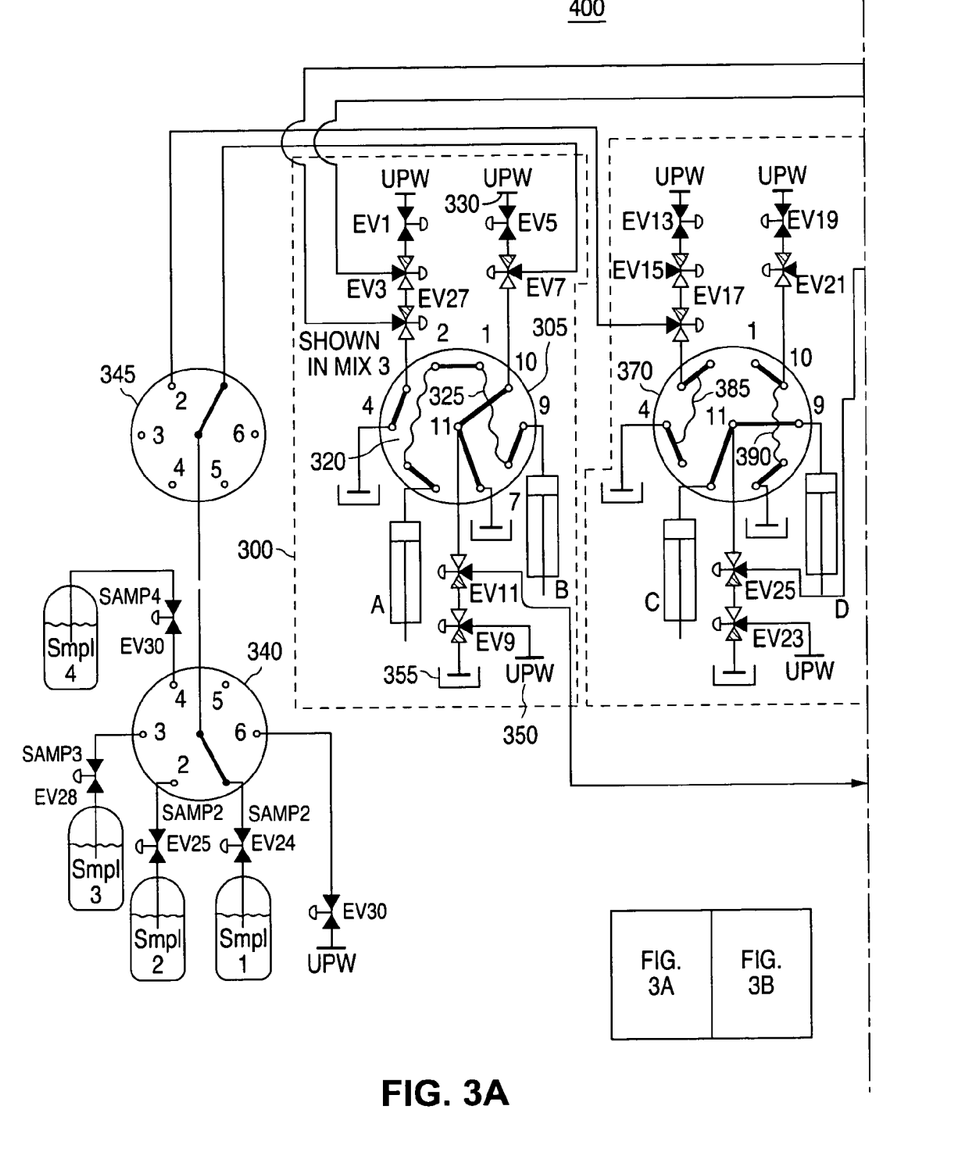
FIG. 3 is a schematic representation of two dilution modules connected to a mass spectrometry instrument according to one embodiment of the invention.
Figure 3B:
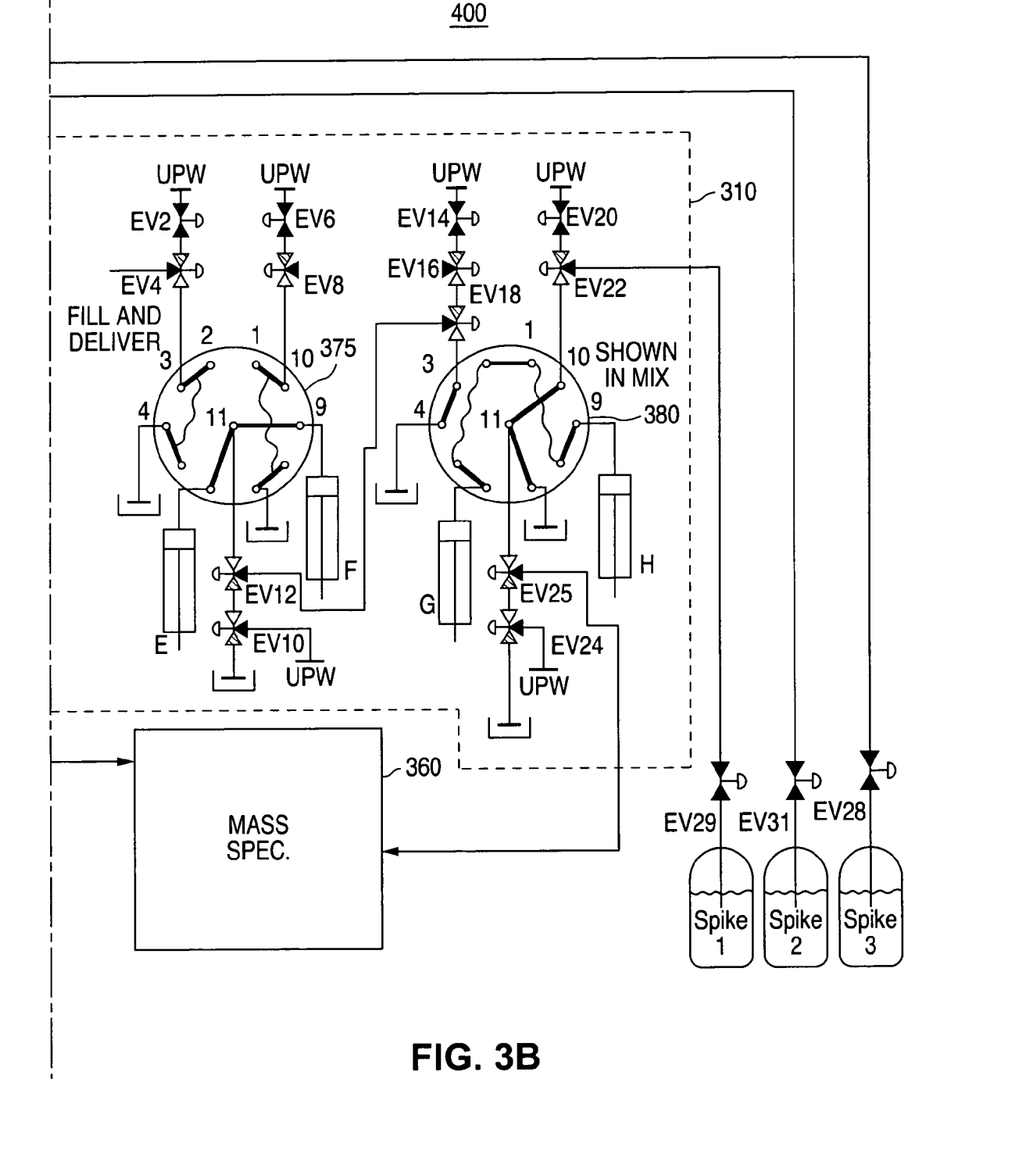

Dilution modules using the dual-loop dilution techniques disclosed herein may be used in various automated metrology instruments. For example, two dilution modules 300 and 310 for an IPMS system 400 are shown in FIG. 3. In this embodiment, the diluent is ultra-pure water (UPW). It will be appreciated, however, that the type of diluent used depends upon the sample being analyzed and the type of metrology instrument used to perform the analysis. Dilution module 300 provides a single stage of dilution using a dual-loop multi-way valve 305. Dilution module 310 provides three stages of dilution using dual-loop multi-way valves 370, 375, and 380. In dilution module 300, dual-loop multi-way valve 305 functions to connect its 11 ports in the same fashion as described with respect to valve 200 of FIGS. 2a and 2b. Thus, in a fill and delivery configuration, a sample fills a first loop 325 whereas a spike fills a second loop 320. To provide flexibility, the introduced sample may be selected from four sample sources: sample 1 through sample 4 through the action of a selection valve 340. Another selection valve 345 determines which dilution module (300 or 310) will receive the selected sample from selection valve 340. Dilution module 300 may select its spike from spike sources spike 2 and spike 3 through the selective actuation of three-way valves EV3 and EV27. The selected spike enters multi-way valve 305 at port 3 and fills loop 320. It will be appreciated that although multi-way valve 305 is illustrated in the mixing configuration it would be configured analogously to the fill and delivery configuration described with respect to FIG. 1a at this point. The sample sources sample 1 through sample 4 and spike sources spike 2 and 3 are pressurized with nitrogen gas so that spike and sample flow into their respective loops. Alternatively, pumps may be used to force these solutions into the loops.

Prior to being filled, each loop 325 and 320 connected to multi-way valve 305 may be flushed with ultra-pure water (UPW). For example, valve EV5 and three-way valve EV7 may be configured to connect UPW source 330 to loop 325 through port 10 when multi-way valve 305 is in the fill and delivery configuration. In this configuration, one or both of the syringes A and B may receive UPW from source 350. To receive UPW from source 350, three-way valves EV9 and EV11 are actuated such that UPW from source 350 may flow into port 11 of multi-way valve 305. If, for example, the plunger for syringe A is then withdrawn, UPW will flow from port 11 into syringe A. Note that prior to being filled with UPW, syringes A and B may be contaminated from a previous fill/delivery and mix cycle. To flush these syringes, syringes A and B are filled with UPW as just described and then three-way valves EV11 and EV9 may be configured to connect syringes A and B to drain 355. By depressing the respective plungers using the associated stepper motors (not illustrated), the contents of syringes A and B will be flushed into drain 355. After reconfiguring valves EV11 and EV9, the appropriate syringe (either syringe A or B or both) may be filled with the desired amount of UPW from source 350 as just described. It will be appreciated that numerous variations may be made to dilution module 305 and still obtain the benefits of the dual-loop mixing and dilution features just described. For example, syringes A and B may be made backflushable. In such a syringe, when the plunger is withdrawn a sufficient amount, a backflush port is exposed. The contents of the syringe may then be flushed directly into the backflush port. In such an embodiment, drain 355 would be unnecessary because the syringes would flush through their backflush ports.

Valve 305 is illustrated in the mix configuration. In this configuration, through the reciprocating action of syringes A and B, the sample which had filled loop 325 and the spike which had filled loop 320 are mixed together and diluted in the same fashion as discussed with respect to FIG. 2b. By placing valve 305 back into the delivery and fill configuration, the resulting spiked and diluted sample may be delivered through action of syringes A and B to a mass spectrometry instrument 360 for analysis. It will be appreciated that additional processing such as matrix removal or pH adjustment may be necessary before analysis by mass spectrometry instrument 360.

Module 310 comprises three dual-loop multi-way valves 370, 375, and 380. Module 310 is configured to initially serially dilute a sample selected by selection valve 340 through the action of valves 370 and 375. If, for example, each valve 370, 375, and 380 is configured to achieve a 100:1 dilution, an overall 1,000,000:1 dilution of the sample may be achieved. Such a relatively large amount of dilution of sample before introduction of spike is useful, for example, in the analysis of copper ion concentration in electroplating bath solution. Because spike is not mixed in valves 370 and 375, these valves could comprise conventional single loop dilution valves as discussed with respect to FIGS. 1a and 1b. However, to provide design flexibility and modularity, valves 370 and 375 may comprise dual or greater than dual loop valves. In a fill and delivery configuration, a sample fills loop 385 in dual loop valve 370 through three-way valve EV17 and port 3. An optional and remaining loop 390 within dual loop 370 is filled with UPW at this stage. In addition, analogous to the operation of dilution module 305, one or both of syringes C and D may also be filled with a predetermined volume of UPW. By shifting its rotor (not illustrated), valve 370 then switches to the mix configuration and the contents of syringes C and/or D mix with and dilute the sample within loop 385 the contents of loop 309. In the subsequent fill and delivery configuration for valve 370, the diluted sample may be pumped through three-way valves EV25 and EV4 into port 3 of dual-loop valve 375. Using syringe pumps E and F, an analogous additional round of dilution with UPW occurs through dual-loop valve 375. When dual-loop valve 380 is in the fill and delivery configuration, the doubly-diluted sample from dual-loop valve 375 may then be pumped through three-way valves EV12 and EV18 into port 3 of dual-loop valve 380. In this configuration, dual-loop valve 380 may also receive a spike from spike source 1 through three-way valve EV22 into port 10. The two loops of valve 380 may then be filled with spike and sample, mixed and diluted in an analogous fashion as discussed with respect to dual-loop valve 305. The diluted and spiked sample may then be pumped through three-way valve EV26 to mass spectrometry instrument 360 for analysis. It will be appreciated that dilution modules 305 and 310 are merely exemplary embodiments—for example, alternate dilution module embodiments may be constructed without the use of three-way valves. Moreover, a serial dilution such as that provided by dilution module 310 may be performed with an arbitrary number of stages rather than just the three stages provided by multi-way valves 370, 375, and 380.

Consider the advantages provided by the automated analysis system 400 shown in FIG. 3. The various valves shown may be electronically or pneumatically actuated and thus be under the control of a state machine or microprocessor. Syringe pumps A through H are accurately controlled by stepper motors. Thus, automated, real-time, and continuous analysis of a variety of samples is enabled. Such a capability is particularly advantageous in semiconductor clean rooms, which typically operate around the clock. Without requiring human intervention that could violate clean room requirements, system 400 may automatically sample, spike, dilute, and mix before analysis. Advantageously, the mixing of spike with sample may occur simultaneously with dilution.

In an IPMS application for analysis of semiconductor copper electroplating solution, dilution module 305 may be used to spike samples to study concentrations of organic plating accelerant or suppressor. A conventional accelerant is bis (3-sulfopropyl) disulfide (SPS) which forms complexes with copper ions in the electroplating solution. These molecular ligands of copper are relatively-strongly reactive and thus act to accelerate the copper deposition process. To study the concentration of SPS, one suitable spike would be an isotopically enriched form of SPS for an IDMS analysis. These isotopically enriched forms of SPS will have the substantially the same chemical behavior passing through an electrospray ionization process and a mass spectrometry instrument as does the original sample of SPS. Thus, whatever degradation occurs in the sample also occurs in the spike. Because the concentration of the spike is known, the concentration of SPS in the sample may be determined from the resulting MS spectrum.

Analogous to the use of an isotopically enriched spike, a chemical analog of the analyte-of-interest may be used as the spike or internal standard. As used herein, a chemical analog of an analyte will be understood to have a different molecular composition than the analyte-of-interest but possess substantially the same chemical behavior in passing through the ionization process and mass spectrometry instrument. For example, with respect to analyzing the concentration of bis (3-sulfopropyl) disulfide within a sample, a suitable chemical analog for use as an internal standard is bis (2-sulfoethyl) disulfide (SES). This chemical analog of SPS differs from SPS in tat the propyl groups in SPS are replaced by ethyl groups. Note that the concentration of bis (2-sulfoethyl) disulfide within the spike or internal standard may be carefully predetermined by a user. In addition, the resulting concentration within the diluted and spiked sample will also be known because the volumes of diluent and the loop volumes are all predetermined. Given this concentration, the concentration for SPS within the original sample may be determined from the MS spectrum. For example, using dilution module 305, a sample of a semiconductor copper electroplating bath may be diluted and spiked with a known concentration of SES to have approximately equal concentrations of SES and SPS after dilution, The copper sulfate matrix in the diluted and spiked sample may then be removed using an appropriate matrix removal module such 2 that described in co-assigned U.S. Pat. application Ser. No. 10/641,946, entitled "Matrix Elimination," concurrently filed herewith, the contents of which are hereby incorporated by reference. A portion of the diluted and spiked sample is then ionized by passing through a mass spectrometer interface (not illustrated) of mass spectrometer 360. For example, one suitable mass spectrometry interface is the Atmospheric Pressure Ionization (API) system described in the '025 application. After ionization, mass spectrometer 360 determines the mass/charge ratio of the ions and their concentrations, Many mass spectrometry techniques may be used to determine the mass/charge ratios. For example, magnetic-sector, time-of-flight, inductively-coupled, or electric quadrupole mass analyzers may all be used with the present invention.

Figure 4:
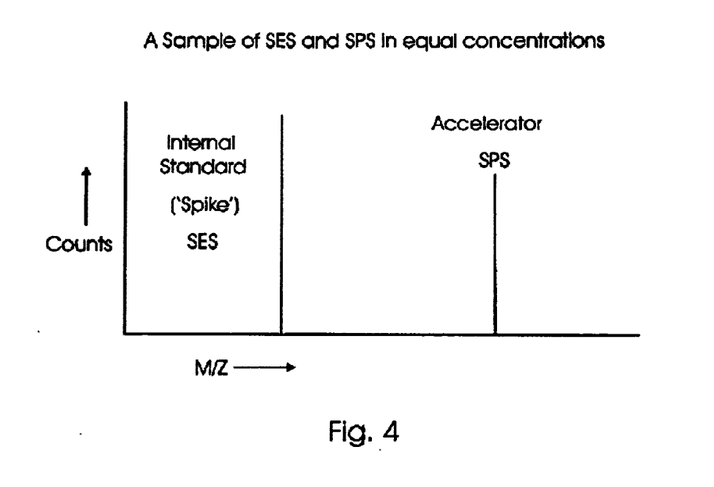
FIG. 4 is a plot of mass-to-charge versus amplitude for the quantification of bis(3-sulfopropyl) disulfide in a sample using an internal standard of bis(2-sulfoethyl) disulfide.

FIG. 4 is a plot of the intensity vs. mass/charge ratio for an ionized SES/SPS mixture using an inductively-coupled mass spectrometer. From FIG. 4, the intensity for the spike or internal standard of SES may be compared to the intensity for SPS. In turn, because the concentration of SES within the diluted and spiked sample of SPS is known, and because the dilution ratio is known, the concentration of SPS may be calculated in the original sample. This calculation is made more accurate if ionization efficiency of SES vs. that of SPS is accounted for—the ionization of SES is greater than that of SPS by a factor of 1.3. Advantageously, the use of a chemical analog as the internal standard or spike obviates the need for relatively expensive preparation of isotopically enriched spikes of analytes of interest.

The above-described embodiments of the present invention are merely meant to be illustrative and not limiting. It will thus be obvious to those skilled in the art that various changes and modifications may be made without departing from this invention in its broader aspects. Accordingly, the appended claims encompass all such changes and modifications as fall within the true spirit and scope of this invention.

What is claimed is:

1. A loop dilution apparatus, comprising:
   a first pump;
   a second pump;

a first reservoir;

a first loop having a predetermined volume;

a second loop having a predetermined volume; and a multi-way valve, wherein the multi-way valve has a first configuration that connects: the first loop to a first solution source, the second loop to a second solution source, and the first pump and the second pump to a diluent source, wherein the first pump is operable to pump diluent from the diluent source into a first reservoir if the multi-way valve is in the first configuration, whereby the first loop is configured to receive a first solution from the solution source and the second loop is configured to receive a second solution from the second source if the multi-way valve is in the first configuration, and wherein the multi-way valve has a second configuration that connects: the first loop to the second loop, the first pump to a first end of the connected loops, and the second pump to a second end of the connected loops, whereby the first pump is configured to pump diluent from the diluent source into the connected loops if the multi-way valve is in the second configuration.

2. The loop dilution apparatus of claim 1, further comprising a second reservoir, wherein the second pump operable to pump diluent from the diluent source into the second reservoir if the multi-way valve is in the first configuration.

3. The loop dilution apparatus of claim 2, wherein the first pump is a first syringe pump, the internal volume of the first syringe pump forming the first reservoir, and wherein the second pump is a second syringe pump, the internal volume of the second syringe pump forming the second reservoir.

4. The loop dilution apparatus of claim 1, further comprising a first drain, wherein the multi-way valve in the first configuration connects the first drain to the first loop such that if the first solution is pumped from the first solution source, the first solution will flush through the first loop into the first drain.

5. The loop dilution apparatus of claim 4, further comprising a second drain, wherein the multi-way valve in the second configuration connects the second drain to the second loop such that if the second solution is pumped from the second solution source, the second solution will flush through the second loop into the second drain.

6. A loop dilution apparatus, comprising:

a plurality of dilution stages arranged from a first stage to a last stage, the first stage being operable to receive a predetermined volume of a first solution and dilute it to form a first diluted solution, the second stage being operable to receive a predetermined volume of the first diluted solution and dilute it to form a second diluted solution, and so on, such that the last stage is operable to receive a first predetermined volume of a next-to-last diluted solution from the next-to-last dilution stage, and wherein the last dilution stage includes:

a first pump;

a first reservoir;

a first loop having the first predetermined volume;

a second loop having a predetermined volume; and a multi-way valve, wherein the multi-way valve has a first configuration connecting a first end of the first loop to a next-to-last dilution stage to receive the first predetermined volume of the next-to-last dilution solution and connecting a first end of the second loop to a second solution source and connecting the first pump to a diluent source, wherein the first pump is operable to pump diluent from the diluent source into the first reservoir if the multi-way valve is in the first configuration, and wherein the multi-way valve has a second configuration serially connecting the first loop to the second loop and connecting the first pump to a first end of the serially-connected loops, whereby the first pump is configured to pump a diluent from the diluent source into the serially-connected loops if the multi-way valve is in the second configuration.

7. The loop dilution apparatus of claim 6, wherein the last dilution stage further comprises:

a second pump, wherein the multi-way valve in the second configuration connects the second pump to a second end of the serially-connected loops.

8. The loop dilution apparatus of claim 7, wherein the last dilution stage further comprises a second reservoir, the second pump being operable to pump diluent from the diluent source into the second reservoir when the multi-way valve is in the first configuration.

9. The loop dilution apparatus of claim 8, wherein the first pump is a first syringe pump, the internal volume of the first syringe pump forming the first reservoir, and wherein the second pump is a second syringe pump, the internal volume of the second syringe pump forming the second reservoir.

* * * * *

UNITED STATES PATENT AND TRADEMARK OFFICE
CERTIFICATE OF CORRECTION

PATENT NO. : 6,998,095 B2
APPLICATION NO. : 10/641480
DATED : February 14, 2006
INVENTOR(S) : Marc R. Anderson et al.

It is certified that error appears in the above-identified patent and that said Letters Patent is hereby corrected as shown below:

On the title page after the abstract "4 Drawing" should read -- 5 Drawing --.

Include attached Fig. 4

Fig. 4

Signed and Sealed this

Nineteenth Day of September, 2006

JON W. DUDAS
*Director of the United States Patent and Trademark Office*